United States Patent
Gervasi et al.

(10) Patent No.: US 6,747,089 B2
(45) Date of Patent: Jun. 8, 2004

(54) PROCESSES FOR SOLUBILIZING ORGANOMETALLIC COMPOUNDS IN FLUORINATED SOLVENTS BY ADDITION OF A FLUORINATED NON-CATALYTIC CO-SOLUBILIZER

(75) Inventors: David J. Gervasi, West Henrietta, NY (US); Santokh S. Badesha, Pittsford, NY (US); George J. Bingham, Savannah, GA (US)

(73) Assignee: Xerox Corporation, Stamford, CT (US)

( * ) Notice: Subject to any disclaimer, the term of this patent is extended or adjusted under 35 U.S.C. 154(b) by 181 days.

(21) Appl. No.: 10/199,927

(22) Filed: Jul. 18, 2002

(65) Prior Publication Data

US 2004/0014862 A1 Jan. 22, 2004

(51) Int. Cl.$^7$ .............................. C08K 5/15; C08K 5/07; C08L 27/12
(52) U.S. Cl. ..................... 524/546; 524/108; 524/354; 524/356; 524/546; 524/555; 524/588; 524/590
(58) Field of Search ................................ 524/546, 108, 524/354, 356, 555, 588, 590

(56) References Cited

U.S. PATENT DOCUMENTS

| | | | |
|---|---|---|---|
| 5,225,561 A | 7/1993 | Kirlin et al. | 546/256 |
| 5,280,012 A | 1/1994 | Kirlin et al. | 505/1 |
| 5,453,494 A | 9/1995 | Kirlin et al. | 534/15 |
| 5,504,195 A | 4/1996 | Leedham et al. | 534/15 |
| 5,892,083 A | 4/1999 | Winter et al. | 556/412 |
| 6,126,996 A | 10/2000 | Kirlin et al. | 427/252 |
| 6,183,872 B1 * | 2/2001 | Tanaka et al. | 428/429 |

OTHER PUBLICATIONS

Liquid ventilation A new way to deliver drugs to diseased lungs?, Lehmer, H., Bummer, P., Jay, M. *CHEMTECH, Oct. 1999*, p. 7–12.

Fluorous Synthesis: A Fluorous–Phase Strategy for Improving Separation Efficiency in Organic Synthesis, Studer, A., Hadida, S., Ferritto, R., Kim, S., Jeger, P. Wipf, P., Curran, D., *Science Magazine*, Feb. 7, 1997 vol. 275, p. 823–826, http://www.sciencemag.org.

Facile Catalyst Separation Without Water: Fluorous Biphase Hydroformylation of Olefins, Horvath, I., Rabal, J., *Science Magazine*, Oct. 7, 1994, vol. 266, p. 72–75.

Facile Catalyst Separation without Water: Fluorous Biphase Hydroformylation of Olefins, Horvath, I.T., Rabal, J., *CHEMTRACTS, Inorganic Chemistry*, 1995, vol. 7, No. 1, p. 14–18.

A Soluble Fluorous Phase Polymer Support, Bergbreiter, D., Franchina, J., *Chem. Commun.*, 1997, p. 1531–1532.

Are Teflon "Ponytails" the Coming Fashion for Catalysts?, Gladysz, J. A., *Science Magazine*, Oct. 7, 1994, vol. 266, p. 55–56.

Solubility Enhancement of Phenol and Phenol Derivatives in Perfluorooctyl Bromide, Williams, T., Jay, M., Lehmler, H., Clark, M., Stalker, D., Bummer, P., *Journal of Pharmaceutical Sciences*, Dec. 1998, vol. 87, No. 12, p. 1585–1589.

Phosphorous (III) ligands in fluorous biphase catalysis, Bhattacharyya, P., Croxtall, B., Fawcett, Joanne, Fawcett, John, Gudmunsen, D., Hope, E., Kemmitt, R., Paige, D., Russell, D., Stuart, A., Wood, D., *Journal of Fluorine Chemistry 101*, 2000, p. 247–255.

The rhodium catalysed hydrogenation of styrene in the fluorous biphase, Hope, E., Kemmitt, R., Paige, D., Stuart, A., Wood, D., *Journal of Fluorine Chemistry 99*, 1999, p. 197–200.

Fluorous biphase catalysis, Hope, E., Stuart, A., *Journal of Fluorine Chemistry 100*, 1999, p. 75–83.

Behavior of partially fluorinated carboxylic acids at the air–water interface, Lehmler, H., Oyewumi, M., Jay, M., Bummer, P., *Journal of Fluorine Chemistry 107*, 2001, p. 141–146.

* cited by examiner

Primary Examiner—Kriellion A. Sanders
(74) Attorney, Agent, or Firm—Annette L. Bade

(57) ABSTRACT

A process for solubilizing an organometallic compound in a fluorinated solvent to form an organometallic solution by adding and reacting a co-solubilizer having a fully fluorinated polymer, an organometallic compound, and a fluorinated solvent, and the co-solubilizer has the ability to cause the organometallic compound to become miscible in a fluorinated solvent, and further, the co-solubilizer is not a catalyst and is present in the final organometallic solution.

21 Claims, No Drawings

PROCESSES FOR SOLUBILIZING ORGANOMETALLIC COMPOUNDS IN FLUORINATED SOLVENTS BY ADDITION OF A FLUORINATED NON-CATALYTIC CO-SOLUBILIZER

CROSS REFERENCE TO RELATED APPLICATIONS

Reference is made to co-pending, commonly-assigned, U.S. patent application Ser. No. 10/137,789, filed May 2, 2002, entitled, "Fully Fluorinated Polymer Coated Development Electrodes;" and, U.S. patent application Ser. No. 10/199,619, filed Jul. 18, 2002, entitled, "Coatings Having Fully Fluorinated Co-Solubilizer, Metal Material and Fluorinated Solvent;" the subject matter each of which is hereby incorporated by reference in its entirety.

BACKGROUND OF THE INVENTION

The present invention relates to methods for solubilizing organometallic compounds in fluorinated solvents by addition of a co-solubilizing agent. In embodiments, the co-solubilizing agent is a fluorinated co-solubilizer. In embodiments, a fluorinated tail is added to an organometallic compound to cause the organometallic compound to become soluble in a fluorinated solvent. In embodiments, the organometallic compound, which is normally not soluble in fluorinated solvents, becomes completely miscible in fluorinated solvents. Such materials can be used in many arts such as, for example, electrical arts, electrostatographic arts, computer arts, and the like. In embodiments, the organometallic compound and fluorinated solvent solution can be useful as, for example, electrically or thermally conductive soluble fluoropolymer-ceramic hybrids or intermediates, electroluminescent fluorinated fluids or polymer coatings, photosensitive fluorinated fluids or coatings, colored fluorinated fluids or soluble polymer coatings for display devices, fluorinated carrier fluids for metal oxide film formation (where low surface tension of fluorinated fluids are desirable), thermochromic fluorescent or electrochromic fluorinated fluids or coatings, wire coatings such as electrode wire coatings, and many other applications.

In embodiments, the fluorinated co-solubilizer does not act as a catalyst, but instead, acts as a filler or additive, and is present in the final solution.

Fluorinated solvents are preferred vehicles for many substances. Fluorinated solvents are preferred because they are thermally insulative, have low surface energy, can have low boiling points, and can be recyclable or recoverable.

A problem results in that many substances are not soluble in fluorinated solvents. For example, many organic molecules and many non-fluorinated or partially fluorinated compounds, are not soluble in fluorinated solvents. Specifically, most, if not all, organometallic compounds, and especially superconductors or superconductor precursors, are not soluble in fluorinated solvents.

Attempts have been made to render previously fluoro-insoluable materials soluble in fluorinated solvents. These attempts include using fluoro-ponytails (e.g., long carbon chains consisting mainly of perfluoroalkyl segments) as co-solvents. These ponytails greatly increase solubility in the fluorous phase. Many approaches are discussed below. However, in all these approaches, the co-solvent is used as a catalyst and can be separated at the end of the reaction.

A paper by the University of Leicester Department of Chemistry (http://www.le.ac.uk/chemistry/research/epsrc/egh1.html, Aug. 28, 2001) entitled, "Catalysis in the Fluorous Biphase," discloses methods for preparation of catalysts derivatised with perfluoroalkyl substitutents to evaluate the criteria for preferential fluorous phase solubility and to investigate the influence of the perfluoroalkyl groups on the properties and activities of the metal catalyst.

A paper from *Chemtech* October 1999 (pp. 7–12) by Hans-Joachim Lehmler et al. entitled, "Liquid Ventiliation—A New Way to Deliver Drugs to Diseased Lungs?," discloses ways of enhancing solubility in perfluorocarbon solvents of drugs.

A paper from *Science*, Vol. 275, Feb. 7, 1997 (pp. 823–826) by Armido Studer et al. entitled, "Fluorous Synthesis: A Fluorous-Phase Strategy for Improving Separation Efficiency in Organic Synthesis" teaches a "fluorous synthesis" approach in which organic molecules are rendered soluble in fluorocarbon solvents by attachment of a suitable fluorocarbon group.

A paper from *Science*, Vol. 266, Oct. 7, 1994 (pp. 72–75) by Istvan T. Horvath et al. entitled, "Facile Catalyst Separation without Water: Fluorous Biphase Hydroformulation of Olefins" discloses the application of fluorous biphase system for the extraction of rhodium from toluene and for the hydroformylation nf olefins.

A paper from *Science*, Vol. 266, Oct. 7, 1994 (pp. 55–56) by J. A. Gladysz, entitled, "Are Teflon "Ponytails" the Coming Fashion for Catalysts?" discusses use of long carbon chains consisting mainly of perfluoroalkyl segments called "ponytails" appended to increase solubility in the fluorous phase and serve as de facto anchors.

A paper from *Chem. Commun.*, 1998 (pp. 1531–1532) by David E. Bergbreiter et al. entitled, "A Soluble Fluorous Phase Polymer Support," discloses preparation of a soluble fluorocarbon polymer that has reactive sites that can be used to covalently bind reagents and to render them soluble in the fluorous phase as a polymer-bound reagent.

A paper from *Journal of Pharmaceutical Sciences*, Vol. 87, No. 12, December 1998 (pp. 1585–1589) by Thomas D. Williams et al. entitled, "Solubility Enhancement of Phenol and Phenol Derivatives in Perfluorooctyl Bromide," discusses examining the use of a hydrophobic solubilizing agent capable of interacting with model drug solutes by hydrogen bonding with the purpose of enhancing solubility in perfluorooctyl bromide.

A paper from *Journal of Fluorine Chemistry* 101, 2000, (pp. 247–255) by Pravat Bhattacharyya et al., entitled "Phosphorus (III) Ligands in Fluorous Biphase Catalysis," discloses the synthesis, coordination chemistry and catalytic applications of a series of perfluoroalkyl-substituted phosphorus (III) ligands.

A paper from *Journal of Fluorine Chemistry* 99, 1999, (pp. 197–200) by Eric G. Hope et al., entitled "The Rhodium Catalyzed Hydrogenation of Styrene in the Fluorous Biphase," discloses the use of rhodium-catalyzed hydrogenation of styrene as a system to study the influence of the perfluorocarbon and organic solvents and the perfluoroalkyl-ponytails on an application of the fluorous biphase approach to homogeneous catalysis.

A paper from *Journal of Fluorine Chemistry* 100, 1999, (pp. 75–83) by Eric G. Hope et al., entitled "Fluorous Biphase Catalysis," discusses the evolution and future prospects for the fluorous biphase approach to homogeneous catalysis.

A paper from *Journal of Fluorine Chemistry* 107, 2001, (pp. 141–146) by Hans-Joachim Lehmler et al., entitled "Behaviour of Partially Fluorinated Carboxylic Acids at the Air-Water Interface," discloses langmuir isotherms for several acids.

A paper from *Chemtracts-Inorganic Chemistry* Vol. 7 1995 (pp. 14–18) by I. T. Horvath et al., entitled, "Facile Catalyst Separation Without Water: Fluorous Biphase Hydroformylation of Olefins," discloses the utility of a new simple scheme to effect catalyst/product separation in homogeneous catalysis.

However, it is sometimes desired that a fluorosolubilizing co-solvent not be used as a catalyst as it is used in the above listed experiments. This is necessary when it is not suitable to include the step of separating the catalyst from the fluorinated solution. Such a situation may include creating a coating by mixing several compounds together.

SUMMARY OF THE INVENTION

Embodiments of the present invention include: a process for solubilizing an organometallic compound in a fluorinated solvent to form an organometallic solution, comprising adding and reacting a co-solubilizer comprising a fully fluorinated polymer, an organometallic compound, and a fluorinated solvent, wherein the co-solubilizer has the ability to cause the organometallic compound to become miscible in a fluorinated solvent, and wherein the co-solubilizer does not react as a catalyst and is present in the organometallic solution.

Embodiments further include: a process for solubilizing an organometallic compound in a fluorinated solvent to form an organometallic solution, comprising adding and reacting a co-solubilizer comprising a fully fluorinated polymer, an organometallic compound selected from the group consisting of a superconductor and superconductor precursor, and a fluorinated solvent, wherein the co-solubilizer has the ability to cause the organometallic compound to become miscible in the fluorinated solvent, and wherein the co-solubilizer is not a catalyst and is present in the organometallic solution.

In addition, embodiments include: a process for solubilizing an organometallic compound in a fluorinated solvent to form an organometallic solution, comprising adding and reacting a co-solubilizer comprising a fully fluorinated polymer, an organometallic compound, and a fluorinated solvent, wherein the co-solubilizer is a copolymer of tetrafluoroethylene and an oxy-halo perfluoropolymer, and wherein the co-solubilizer has the ability to cause the organometallic compound to become miscible in the fluorinated solvent, and further wherein the co-solubilizer does not act as a catalyst and is present in the organometallic solution.

DETAILED DESCRIPTION

The present invention relates to methods for solubilizing organometallic compounds in fluorinated solvents by addition of a co-solubilizing agent. In embodiments, the co-solubilizing agent is a fully fluorinated co-solubilizer. In embodiments, a fluorinated tail is added to an organometallic compound to render soluble the organometallic compound in a fluorinated solvent. In embodiments, the orqanometallic compound, which is normally not soluble in fluorinated solvents, becomes completely miscible in fluorinated solvents due to the addition of the fully fluorinated co-solubilizer. In embodiments, the fluorinated co-solubilizer does not act as a catalyst, but instead, acts as a filler or additive, and is present in the final organometallic composition. In embodiments, a co-solubilizer comprises a fully fluorinated polymer.

The term "fully fluorinated polymers" as used herein, refers to fluorinated polymers that do not contain any hydrocarbon chains, hydrocarbon units, hydrocarbon substituents, or any carbon-hydrogen bonds. The term "fully fluorinated polymers" includes polymers comprising fluorinated monomers containing no hydrocarbon units, and monomers that are fully fluorinated and do not contain any hydrocarbon units. In embodiments, the fully fluorinated polymers are soluble in fluorinated solvents. In embodiments, the fully fluorinated polymers may be amorphous, thereby giving them excellent light transmission properties. In embodiments, the fully fluorinated polymers are solution-coatable and have a low surface energy, and therefore, smooth, thin and uniform low surface energy coatings can result.

A co-solubilizer is a substance, which when added to a mixture renders the solute of that mixture soluble by reaction with the solute. A co-solubilizer is normally soluble in the solvent. Without the co-solubilizer, the solute would otherwise not be soluble in the solvent.

Examples of suitable co-solubilizers comprising a fully fluorinated polymer include perfluorinated siloxanes, perfluorinated styrenes, perfluorinated urethanes, copolymers of fluoropolymers and perfluoropolymers such as, copolymers of tetrafluoroethylene and fully fluorinated polymers, and copolymers of tetrafluoroethylene and oxygen-containing fully fluorinated polymers, copolymers of tetrafluoroethylene and oxy-halo-fully fluorinated fluoropolymers, and mixtures thereof.

In embodiments, the fully fluorinated polymer comprises the following Formula I:

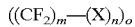

wherein m is a number of from about 1 to about 100, or from about 2 to about 50, or from about 5 to about 25; n is a number of from about 1 to about 100, or from about 2 to about 50, or from about 5 to about 25; and o is a number of from about 1 to about 100, or from about 2 to about 50, or from about 5 to about 25; and wherein X is selected from the group consisting of unsubstituted or substituted, straight or branched chain fluorocarbons having from about 1 to about 50 fluorocarbons, or from about 2 to about 25 fluorocarbons; substituted or unsubstituted cyclic fluorocarbons having from about 3 to about 20 fluorocarbons, or from about 4 to about 10 fluorocarbons; and substituted or unsubstituted oxy-halo fluorocarbons having from about 3 to about 10 fluorocarbons, or from about 4 to about 6 fluorocarbons. Other possible substituents for X include hexafluoropropylene, and/or perfluoroalkoxy-substituted tetrafluoroethylene.

In embodiments, the polymer has the following Formula II:

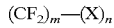

wherein m, n and X are as defined in Formula I.

In embodiments, the fully fluorinated polymer has the following Formula III:

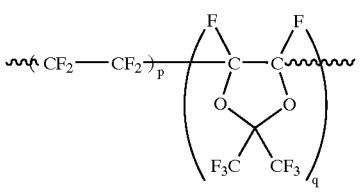

wherein p is a number of from about 1 to about 100, or from about 2 to about 50, or from about 5 to about 25; and q is a number of from about 1 to about 100, or from about 2 to about 50, or from about 5 to about 25. A commercially available perfluoropolymer having the above Formula III is TEFLON® AF, a copolymer of tetrafluoroethylene and perfluoro-2,2-dimethyl-1,3-dioxide, the latter monomer being fully fluorinated.

In embodiments, the fully fluorinated polymer has the following Formula IV:

$$((CF_2)_m\text{—}X\text{—}(CF_2)_r)_o$$

wherein r is a number of from about 0 to about 50, or from about 1 to about 25, or from about 2 to about 15; and wherein X, m and o are as defined for Formula I.

In embodiments, the fully fluorinated polymer has the following Formula V:

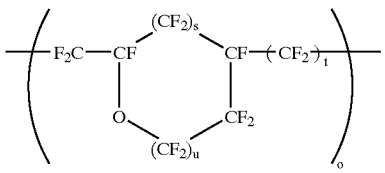

wherein o is as defined in Formula I, s is a number of from about 0 to about 5, or from about 1 to about 3, or 2; t is a number of from about 0 to about 25, or from about 1 to about 15, or from about 5 to about 10; and u is a number of from about 0 to about 5, or from about 1 to about 3, or 2. A commercially available example of a perfluoropolymer having the above Formula IV is CYTOP® available from Asahi Glass Company.

Another specific example of a fully fluorinated material co-solubilizer is AUSIMONT® Fluorolink F7004 from Ausimont, Thorofare, N.J. This fully fluorinated polymer is useful in solubilizing organometallic compounds in fluorinated solvents. This fully fluorinated polymer works well with copper complexes such as copper (ii) hexafluoropentanedionate.

The fully fluorinated coating material is present in the organometallic solution in an amount of from about 0.1 to about 40 percent by weight of total solids, or from about 2 to about 15 percent by weight of total solids. Total solids as used herein, refers to the total amount by weight of fully fluorinated material, fillers, additives, organometallic material such as superconductor or superconductor precursor, and other like solid ingredients contained in the organometallic solution.

An organometallic compound may be used herein in the process. In embodiments, the organometallic compound can be a superconductor or superconductor precursor. The term "superconductors" as used herein refers to metals, alloys and compounds which have the ability to lose both electrical resistance and magnetic permeability at or near absolute zero. In other words, superconductors have infinite electrical conductivity at or near absolute zero. Superconductivity does not normally occur in alkali metals, noble metals, ferro- and antiferromagnetic metals. Usually, elements having 3, 5, or 7 valence electrons per atom can be superconductors.

A superconductor precursor is a material that may be processed to form a superconductor. Organometallic compounds are typically processed via chemical vapor deposition (CVD) to produce films which can be either superconductors or can possess other unique properties such as chemochromic or thermochromic properties. MOCVD refers to metal-organic chemical vapor deposition. Organometallics that can be processed to create superconductor films are referred to as superconductor precursors.

Other examples of suitable superconductors include metal oxide superconductors comprising admixtures of metals from Groups IB, IIA, and IIIB of the Periodic Table. Illustrative materials of such type include the metal oxide superconductors of the yttrium-barium-copper type ($YBa_2Cu_3O_y$) type, the so-called "123" high temperature superconductors (HTSC) materials, wherein y may be from about 6 to about 7.3, as well as materials where Y may be substituted by Nd, Sm, Eu, Gd, Dy, Ho, Yb, Lu, $Y_{0.5}$—$Sc_{0.5}$, $Y_{0.5}$—$La_{0.5}$, and $Y_{0.5}$—$Lu_{0.5}$, and where Ba may be substituted by Sr—Ca, Ba—Sr, and Ba—Ca. Another illustrative class of superconductor materials includes those of the general formula $(AO)_mM_2Ca_{n-1}Cu_nO_{2n+2}$, wherein the A cation can be thallium, lead, bismuth, or a mixture of these elements, m=1 or 2 (but is only 2 when A is bismuth), n is a number of from about 1 to about 5, M is a cation such as barium or strontium, and the substitution of calcium by strontium frequently is observed, as described in "High Tc Oxide Superconductors," MRS Bulletin, January, 1989, pp. 20–24, and "High Tc Bismuth and Thallium Oxide Superconductors," Sleight, A. W., et al., MRS Bulletin, January, 1989, pp. 45–48. Other examples include $YbBa_2Cu_3O_{7-x}$ (see P. P. Edwards et al. *Chemistry Britain*, 1987, pp. 23–26; $Pb_2Sr_2LnCu_3)O_{8-x}$ (see M. O'Keefe et al., *J. Am. Chem. Soc.* 1988, 110, 1506; $La_{2-x}Sr_xCuO_4$ (see Bednorz and Muller, *Z. Phys. B. Cond. Matter,* 1986, 64, pp 189–195, and the like.

Specific examples of superconductors or superconductor precursors include organometallic compounds such as copper (II) hexafluoropentanedionate, copper (II) methacryloxyethylacetonacetate, antimony ethoxide, indium hexafluoropentandionate, and the like, and mixtures thereof.

Other organometallic fillers include monodentate, bidentate, or multidentate ligands such as beta-diketonates, cyclopentadienyls, alkyls, perfluoroalkyls, alkoxides, perfluoroalkoxides, and Schiff bases. Other examples of bidentate or multidentate ligands may comprise oxyhydrocarbyl ligands, nitrogenous oxyhydrocarbyl ligands, or fluorooxyhydrocarbyl ligands. The multidentate ligand may be selected from the group consisting of amines and polyamines, bipyridines, ligands of the Formula IV:

wherein G is —O—, —S—, or —NR—, wherein R is H or hydrocarbyl; crown ethers or cryptates; and ligands of the formula $R^0O(C(R^1)_2C(R^2)_2O)_nR^0$, wherein $R^0$ is selected from the group consisting of hydrogen, methyl, ethyl, n-propyl, cyanato, perfluoroethyl, perfluoro-n-propyl, or vinyl; $R^1$ is hydrogen, fluorine, or a sterically acceptable hydrocarbyl substituent; $R^2$ is hydrogen, fluorine or a sterically acceptable hydrocarbyl substituent; n is 4, 5, or 6, and $R^0$, $R^1$ and $R^2$ may be the same or different from each other.

Examples of organometallic additives also include those having the following Formula VII:

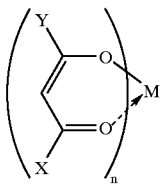

where M may be selected from the group consisting of Al, Ba, Be, Bi, Cd, Ca, Ce, Cr, Co, Cu, Ga, Hf, In, Ir, Fe, Pb, Li, Mg, Mn, Mo, Ni, Pd, Pt, K, Dy, Er, Eu, Gd, Ho, La, Nd, Pr, Sm, Sc, Tb, Tm, Yb, Y, Rh, Ru, Si, Ag, Na, Sr, Ta, Tl, Sn, Ti, V, Zn, Zr, and the like; X or Y may be a hydrocarbon chain having from about 1 to about 30 carbons, or from about 3 to about 12 carbons; a fluorocarbon having from about 1 to about 30 carbons or from about 3 to about 12 carbons, or having from about 1 to about 20 fluorocarbon units of from about 3 to about 8 fluorocarbon units; a substituted or unsubstituted alkoxy group such as methoxy, propoxy, ethoxy, butoxy, pentoxy, and the like; substituted or unsubstituted a cyclic group having from about 4 to about 12 carbons such as cyclobutane, cyclopentane, benzene, a phenyl group such as phenol, cycloheptane, and the like; and wherein n is a number of from about 1 to about 100, or from about 1 to about 20, or from about 1 to about 4.

The organometallic compound can be present in the organometallic solution in any desired amount. Examples of amounts include from about 10 to about 250 parts per hundred, or from about 25 to about 200 parts per hundred, or from about 50 to about 200 parts per hundred organometallic material:polymer.

Any suitable fluorinated solvent may be used. A fluorinated solvent is a solvent comprising fluorine. In embodiments, the fluorinated solvent has low surface energy and low surface tension. Examples of fluorinated solvents include any partially fluorinated organic molecule with having a carbon chain with from about 2 to about 25 carbons, or from about 5 to about 15 carbons. The fluorinated solvent may contain carboxylic acid functionality. A specific commercially available example of a suitable fluorinated solvent includes Fluorinert FC-75 from 3M. The fluorinated solvent is added to the organometallic compound and the fully fluorinated polymer in an amount of from about 1 to about 20 percent, or from about 5 to about 15 percent solution by weight.

The process for solubilizing an organometallic compound in a fluorinated solvent to form an organometallic solution includes adding and reacting a co-solubilizer, an organometallic compound, and a fluorinated solvent. Unlike in known processes, the co-solubilizer does not act like a catalyst. Instead, the co-solubilizer acts as a filler or additive, and is present in the final organometallic solution. In known processes, fluorinated co-solubilizers act as catalysts and are not "used up" in the reaction, and do not become part of the final solution. Instead, in known processes, the fluorinated co-solubilizers can be easily and readily separated out of the final solution. In the present process, the fluorinated co-solubilizer is "used up" in the process, is present in the final solution, and is not readily or easily separated out of the final solution. The fluorinated solvent in the present process has the ability to cause the organometallic compound or superconductor to become miscible in the fluorinated solvent.

In known processes of fluorous biphase catalysis, the organometallic compound is solubilized in the fluorinated solvent via similar methods described here. The catalysis reaction occurs when an aqueous phase (containing reactants) is combined into one single phase at a temperature at which the aqueous phase and a given fluorinated solvent phase are miscible. When the reaction is completed, the temperature of the reaction vessel is then returned to a temperature where the aqueous and fluorinated phase are once again immiscible. The catalyst remains in the fluorinated phase where it can be re-used, while the product of the reaction is emulsified or soluble in the aqueous phase.

All the patents and applications referred to herein are hereby specifically and totally incorporated herein by reference in their entirety in the instant specification.

The following Examples further define and describe embodiments of the present invention. Unless otherwise indicated, all parts and percentages are by weight.

EXAMPLES

Example 1

Preparation of Multidentate Ligand in Fluorinated Solvent Solution

An amount of 0.05 grams (0.0001 moles) of an organometallic bidentate ligand (copper II hexafluoropentanedionate) was added to 5.0 grams of 3M Fluorinert FC-75 (a fluorinated solvent). At this point, the superconductor precursor (CuHFP) was not soluble in the fluorinated solvent.

Example 2

Solubilization of Multidentate Ligand in Fluorinated Solvent Solution

To the mixture formed in Example 2, an amount of 0.5 g (approximately 0.0008 moles) of Ausimont Fluorolink 7004 (fully fluorinated co-solubilizer) was added. The resulting combination formed a green-blue solution.

The CuHFP was insoluble in FC-75 (fluorinated solvent) until the Fluorolink F7004 (fully fluorinated co-solubilizer) was added.

Example 3

Solubilization of Multidentate Ligand in Fluorinated Solvent Solution

To the solution formed in Example 2, an amount of 5 grams of a 1 weight percent solution of a fully fluorinated polymer (TEFLON® AF 2400) in a fluorinated solvent (FC-75) was added. The resulting solution was blue-green and exhibited no signs of insolubility or immiscibility.

While the invention has been described in detail with reference to specific and preferred embodiments, it will be appreciated that various modifications and variations will be apparent to the artisan. All such modifications and embodiments as may readily occur to one skilled in the art are intended to be within the scope of the appended claims.

What is claimed is:

1. A process for solubilizing an organometallic compound in a fluorinated solvent to form an organometallic solution, comprising adding and reacting a co-solubilizer comprising a fully fluorinated polymer, an organometallic compound, and a fluorinated solvent, wherein said co-solubilizer has the ability to cause said organometallic compound to become miscible in a fluorinated solvent, and wherein said co-solubilizer does not react as a catalyst and is present in the organometallic solution.

2. A process in accordance with claim 1, wherein said co-solubilizer is selected from the group consisting of perfluorinated siloxanes, perfluorinated styrenes, perfluorinated urethanes, and copolymers of tetrafluoroethylene and a perfluoropolymer.

3. A process in accordance with claim 2, wherein said substituent is a copolymer of tetrafluoroethylene and an oxy-halo perfluoropolymer.

4. A process in accordance with claim 1, wherein said fully fluorinated polymer has the following Formula I:

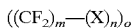

$((CF_2)_m-(X)_n)_o$ wherein m is a number of from about 1 to about 100, n is a number of from about 1 to about 100, and o is a number of from about 1 to about 100, and wherein X is selected from the group consisting of straight chain fluorocarbons having from about 1 to about 50 fluorocarbons; branched fluorocarbons having from about 1 to about 50 fluorocarbons; cyclic fluorocarbons having from about 3 to about 20 fluorocarbons; and oxy-halo fluorocarbons having from about 3 to about 10 fluorocarbons.

5. A process in accordance with claim 4, wherein m is a number of from about 2 to about 50, n is a number of from about 2 to about 50, and o is a number of from about 2 to about 50.

6. A process in accordance with claim 4, wherein X is an oxy-halo fluorocarbon having from about 3 to about 10 fluorocarbons.

7. A process in accordance with claim 1, wherein said fully fluorinated polymer has the following Formula II:

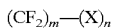

$(CF_2)_m-(X)_n$ wherein m is a number of from about 1 to about 100, n is a number of from about 1 to about 100, and wherein X is selected from the group consisting of straight chain fluorocarbons having from about 1 to about 50 fluorocarbons; branched fluorocarbons having from about 1 to about 50 fluorocarbons; cyclic fluorocarbons having from about 3 to about 20 fluorocarbons; and oxy-halo fluorocarbons having from about 3 to about 10 fluorocarbons.

8. A process in accordance with claim 7, wherein X in Formula II is an oxy-halo fluorocarbon having from about 3 to about 10 fluorocarbons.

9. A process in accordance with claim 7, wherein said fully fluorinated polymer has the following Formula III:

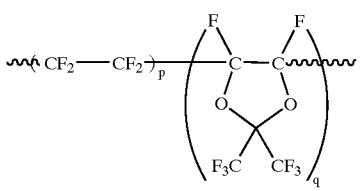

wherein p is a number of from about 1 to about 100, and q is a number of from about 1 to about 100.

10. A process in accordance with claim 9, wherein said fully fluorinated polymer is a copolymer of tetrafluoroethylene and perfluoro-2,2-dimethyl-1,3-dioxide.

11. A process in accordance with claim 1, wherein said fully fluorinated polymer has the following Formula IV:

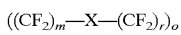

$((CF_2)_m-X-(CF_2)_r)_o$ wherein m is a number of from about 1 to about 100, o is a number of from about 1 to about 100, r is a number of from about 0 to about 50, and wherein X is selected from the group consisting of straight chain fluorocarbons having from about 1 to about 50 fluorocarbons; branched fluorocarbons having from about 1 to about 50 fluorocarbons; cyclic fluorocarbons having from about 3 to about 20 fluorocarbons; and oxy-halo fluorocarbons having from about 3 to about 10 fluorocarbons.

12. A process in accordance with claim 11, wherein said fully fluorinated polymer has the following Formula V:

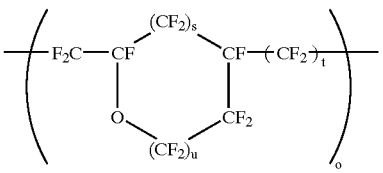

wherein o is a number of from about 1 to about 100, s is a number of from about 0 to about 5, t is a number of from about 0 to about 25, and u is a number of from about 0 to about 5.

13. A process in accordance with claim 1, wherein said organometallic compound is selected from the group consisting of monodentate, bidentate, and multidentate ligands.

14. A process in accordance with claim 1, wherein said organometallic compound is selected from the group consisting of a superconductor and a superconductor precursor.

15. A process in accordance with claim 14, wherein said organometallic compound is selected from the group consisting of copper (II) hexafluoropentanedionate, copper (II) methacryloxyethylacetonacetonate, antimony ethoxide, indium hexafluoropentandionate, and mixtures thereof.

16. A process in accordance with claim 15, wherein said organometallic compound is copper II hexafluoropentanedionate.

17. A process in accordance with claim 1, wherein said fluorinated solvent is a partially fluorinated organic molecule.

18. A process in accordance with claim 1, wherein said fluorinated solvent has from about 2 to about 25 carbons.

19. A process in accordance with claim 1, wherein said fluorinated solvent contains carboxylic acid functionality.

20. A process for solubilizing an organometallic compound in a fluorinated solvent to form an organometallic solution, comprising adding and reacting a co-solubilizer comprising a fully fluorinated polymer, an organometallic compound selected from the group consisting of a superconductor and superconductor precursor, and a fluorinated solvent, wherein said co-solubilizer has the ability to cause said organometallic compound to become miscible in a fluorinated solvent, and wherein said co-solubilizer is not a catalyst and is present in the organometallic solution.

21. A process for solubilizing an organometallic compound in a fluorinated solvent to form an organometallic solution, comprising adding and reacting a co-solubilizer comprising a fully fluorinated polymer, an organometallic compound, and a fluorinated solvent, wherein said co-solubilizer is a copolymer of tetrafluoroethylene and an oxy-halo perfluoropolymer, and wherein said co-solubilizer has the ability to cause said organometallic compound to become miscible in a fluorinated solvent, and further wherein said co-solubilizer does not act as a catalyst and is present in the organometallic solution.

* * * * *